United States Patent [19]

Groman et al.

[11] Patent Number: 5,102,652
[45] Date of Patent: Apr. 7, 1992

[54] LOW MOLECULAR WEIGHT CARBOHYDRATES AS ADDITIVES TO STABILIZE METAL OXIDE COMPOSITIONS

[75] Inventors: Ernest V. Groman, Brookline; Lee Josephson, Arlington, both of Mass.

[73] Assignee: Advanced Magnetics Inc., Cambridge, Mass.

[21] Appl. No.: 475,618

[22] Filed: Feb. 6, 1990

Related U.S. Application Data

[63] Continuation-in-part of Ser. No. 244,432, Sep. 14, 1988, Pat. No. 4,951,675, which is a continuation of Ser. No. 67,586, Jun. 26, 1987, Pat. No. 4,827,945, which is a continuation-in-part of Ser. No. 882,044, Jul. 3, 1986, Pat. No. 4,770,183.

[51] Int. Cl.⁵ .................. G01N 31/00; G01N 24/00; A61K 31/70; A61K 37/00
[52] U.S. Cl. .......................... 424/9; 436/173; 514/12; 514/23; 514/54; 514/59; 514/738; 514/814; 424/617; 424/614
[58] Field of Search .................. 424/9, 617, 646; 436/173; 128/653 CA, 653 AF, 654; 514/12, 54, 59, 23, 738, 814

[56] References Cited

U.S. PATENT DOCUMENTS

| | | | |
|---|---|---|---|
| Re. 24,642 | 4/1959 | London et al. | 167/68 |
| 2,820,740 | 1/1958 | London et al. | 167/68 |
| 2,885,393 | 5/1959 | Herb | 268/209 |
| 3,794,722 | 2/1974 | Taya | 424/647 |
| 3,990,981 | 11/1987 | Kovac et al. | 252/62.54 |
| 4,019,994 | 4/1987 | Kelley | 252/62.52 |
| 4,069,306 | 1/1978 | Rothman | 424/4 |
| 4,101,435 | 7/1978 | Hasegawa et al. | 252/62.53 |
| 4,208,294 | 6/1980 | Khalafalla et al. | 252/62.52 |
| 4,385,046 | 5/1983 | Milbrath et al. | 424/1.1 |
| 4,453,773 | 6/1984 | Molday | 424/1.1 |
| 4,501,726 | 2/1985 | Schröder et al. | 424/1.1 |
| 4,675,173 | 6/1987 | Widder | 424/9 |
| 4,695,392 | 9/1987 | Whitehead et al. | 252/62.54 |
| 4,719,098 | 1/1988 | Weinmann et al. | 424/9 |
| 4,731,239 | 3/1988 | Gordon | 424/9 |
| 4,744,760 | 5/1988 | Molday | 424/3 |
| 4,752,479 | 6/1988 | Briggs et al. | 424/472 |
| 4,770,183 | 9/1988 | Groman et al. | 128/654 |
| 4,786,518 | 11/1988 | Nakel et al. | 426/531 |
| 4,795,698 | 1/1989 | Owen et al. | 435/4 |
| 4,827,945 | 5/1989 | Groman et al. | 128/654 |
| 4,863,715 | 9/1989 | Jacobsen et al. | 424/9 |
| 4,951,675 | 8/1990 | Groman et al. | 128/653 LA |

FOREIGN PATENT DOCUMENTS 8505554 12/1985 World Int. Prop. O. .

OTHER PUBLICATIONS

Rosensweig, R. E., "Magnetic Fluids", *Scientific American*, pp. 136-145 (Oct. 1982).
Magin, R. L., et al., "Dextran Magnetite as a Liver Contrast Agent", *Society for Magnetic Resonance in Medicine*, p. 538 (1987).
Widder, D. J. et al., "Magnetite Albumin Microspheres: A New MR Contrast Agent", *AJR* 148:399-404 (1987).
Hemmingsson, A., et al., "Relaxation Enhancement of the Dog Liver and Spleen by Biodegradable Superparamagnetic Particles in Proton Magnetic Resonance Imaging", *Acta Radiologica* 28(6):703-705 (1987).
Mishler, J. M., "Synthetic Plasma Volume Expanders—Their Pharmacology, Safety and Clinical Efficacy", *Clinics in Haemotology* 13:75-92 (1984).
"Stability Calculations", *Chemical Pharmaceuticals: A Handbook for Pharmacists*, Second Edition, ch. 2 (Connors, K. A. et al. eds. 1986).
Freifelder, David, "Miscellaneous Methods", *Physical Biochemistry*, pp. 518-520 (1976).

*Primary Examiner*—Glennon H. Hollrah
*Assistant Examiner*—Gary E. Hollinden
*Attorney, Agent, or Firm*—Pennie & Edmonds

[57] ABSTRACT

This invention relates to compositions comprising a colloidal or particular metal oxide which are stabilized by low molecular weight carbohydrates. The carbohydrates are characterized by the fact that a) they are not retained on the surface of the metal oxide based on the equilibrium room temperature dialysis of about 2 ml of the metal oxide composition at 0.2 M metal concentration against deionized water; and b) they impart sufficient stability to the metal oxide compositions such that the compositions can withstand heat stress without perceptible aggregation as determined by a prescribed test procedure.

22 Claims, No Drawings

LOW MOLECULAR WEIGHT CARBOHYDRATES AS ADDITIVES TO STABILIZE METAL OXIDE COMPOSITIONS

CROSS-REFERENCE TO RELATED APPLICATIONS

The present application is a continuation-in-part of prior co-pending U.S. application Ser. No. 07/244,432, filed Sept. 14, 1988, now U.S. Pat. No. 4,951,675 which is a continuation of prior U.S. application Ser. No. 067,586, filed June 26, 1987, now U.S. Pat. No. 4,827,945 which, in turn, is a continuation-in-part of prior U.S. application Ser. No. 882,044, filed July 3, 1986, now U.S. Pat. No. 4,770,183. The full disclosures of these prior applications and/or patents are incorporated herein by reference.

1. BACKGROUND OF THE INVENTION

1.1 TECHNICAL FIELD

This invention relates to compositions comprising a colloidal or particulate metal oxide dissolved or suspended in a liquid carrier to which a soluble low molecular weight carbohydrate has been added. It has been discovered that the low molecular weight carbohydrate imparts significant stability to the compositions over a wide range of conditions without modifying the surface of the metal oxide. As such, the low molecular weight additives are useful in the formulation of diverse metal oxide products, including magnetic resonance contrast agents, anemia-treating pharmaceuticals and ferrofluids.

1.2 BACKGROUND ART

The advent of magnetic resonance imaging in medicine has led to the investigation of a wide range of materials as magnetic resonance (MR) contrast agents. Some of the materials investigated are colloidal or particulate in nature. When colloidal or particulate materials are used as parenteral MR contrast agents, the presence of large particles or aggregates can be life-threatening to the subject recipient. In addition, considerations of consumer convenience, and the economic desirability of manufacturing a small number of large lots, require both a long shelf life and the storage of the colloid/particulate materials at ambient temperatures. The development of commercial parenteral MR contrast agents based on colloidal and particulate active ingredients requires that the desirable physical properties of the colloid/particulate material be maintained over a wide range of conditions.

So-called lyophobic colloids and particulate solutions (colloids/particulates with water repelling surfaces) exhibit a general tendency to form high molecular weight aggregates or frank particles upon storage. An example of this phenomenon includes the observation of aggregate formation when superparamagnetic iron oxide is subjected to autoclaving conditions (see FIG. 5 of U.S. Pat. No. 4,827,945 incorporated above by reference). Addition of a polycarboxylate, such as citrate, prevents this undesirable aggregation. However, it is difficult to make the citrate-stabilized fluids isotonic. An advantage of the low molecular weight carbohydrate stabilizers of the current invention is that they can be used to adjust the osmotic pressure of the administered fluid over a wide range. In particular, they can be added to produce an isotonic fluid.

A common approach to the problem of instability in lyophobic colloids and particulate solutions involves the binding of certain agents to the surface of the colloid or particulate, so as to provide increased compatibility between the very large surface area of the colloid/particulate (i.e., large surface area per gram of colloid/particulate) and the solvent. This compatibility between surface and solvent leads to increased stability of the colloid/particulate upon autoclaving and/or storage. Polymeric, high molecular weight agents such as dextran (Hasegawa et al., U.S. Pat. No. 4,101,435; Molday, U.S. Pat. No. 4,452,773 both incorporated herein by reference), bovine serum albumin (Owen, U.S. Pat. No. 4,795,698 incorporated herein by reference) and organosilane (Whitehead, U.S. Pat. No. 4,695,392 incorporated herein by reference) have been used to coat (or otherwise associate with) and presumably to stabilize colloid/particulate solutions. Currently known polymeric stabilizing agents typically have molecular weights above about 5,000 daltons. However, one significant problem encountered in the association of polymers with the surface of the colloid or particulate is that the polymers frequently dissociate from the surface upon prolonged storage or under high temperatures. Such dissociation directly and significantly decreases the stability of the colloid/ particulate solutions.

Dextran/magnetite is an example of a particulate solution specifically noted to be stabilized by the polymeric dextran (see Hasegawa et al., U.S. Pat. No. 4,101,435, column 4, lines 9-43). Several workers have used dextrans of various molecular weights as ingredients in the synthesis of magnetic colloids or particles (see Hasegawa et al., U.S. Pat. No. 4,101,435; Molday, U.S. Pat. No. 4,454,773; Schroder U.S. Pat. No. 4,501,726 incorporated herein by reference). The resulting complexes of dextran and iron oxide have varying sizes and structures, but all have molecular weights of at least about 500,000 daltons. The incorporation of high molecular weight dextran into magnetic particles or colloids may, however, cause some patients to experience adverse reactions to the dextran, when such complexes are administered as parenteral MR contrast agents. These adverse reactions may also in part be due to the previously discussed problem of the high molecular weight polymers such as dextran which dissociate from the metal oxide colloid or particle upon prolonged storage or under high temperatures, leaving the metal oxide free to aggregate.

Similarly, a stable colloidal complex of ferric hydroxide and partially depolymerized dextran has been used in the treatment of iron-deficiency aneamia (Herb, U.S. Pat. No. 2,885,393; London, et al., U.S. Pat. No. 2,820,740 and U.S. Pat. No. Re. 24,642 all incorporated herein by reference). The most suitable range in molecular weight of the partially depolymerized dextran for injection was found to be 30,000 to 80,000 daltons or lower. (Herb, U.S. Pat. No. 2,885,393 col. 2 line 1-7).

Ferrofluids involve another example of the stabilization of magnetic colloids/particulates through surface modification. Typically, low molecular weight (less than 5,000 daltons) detergents are bound to the surface of a particulate solution of magnetic iron oxide (Rosensweig, R., Scientific American, October 1982, pp. 136-145; Khalafalla, U.S. Pat No. 4,208,294; Kovac U.S. Pat. No. 3,990,981, all incorporated herein by reference).

A final approach to the stabilization of colloids involves the addition of polymeric agents to the solvent. Such agents can adsorb to the surface of the colloid in a weak, reversible fashion, changing the surface characteristics sufficiently to enhance stability. There are several problems with adding free polymer as a stabilizing agent for colloids, and in particular for the stabilization of colloids or particles for parenteral administration (e.g., injection). First, upon storage the free polymer may aggregate, producing a liquid with unacceptable physical properties. This aggregation can occur when a polymeric stabilizer is employed that is capable of gelation or aggregation over the storage period. Polymers that have been used for stabilizing colloids that exhibit the property of gelation are gelatin and high molecular weight dextran. Second, after injection, adverse reactions to free polymer are possible. For example, injection of dextran as a plasma expander is associated with adverse reactions (Mishler, J. H., Clinics in Haemotology 13:75–92 (1984) incorporated herein by reference).

2. SUMMARY OF THE INVENTION

Accordingly, an object of this invention is to provide a method of stabilizing colloidal or particulate metal oxide compositions without significant surface modification of the metal oxide.

A further object of this invention is to provide colloidal or particulate metal oxide compositions useful as parenteral MR contrast agents in animal and human subjects which are highly stable to prolonged storage and autoclaving.

A still further object of this invention is to provide parenterally administrable colloidal or particulate iron oxide compositions useful in the treatment of iron anemia in animal and human subjects and which are highly stable to prolonged storage and autoclaving.

A still further object of this invention is to provide improved, stable water-based ferrofluid compositions for use in non-medical applications.

These and other objects are achieved by the addition of an effective amount of certain soluble low molecular weight carbohydrates to the liquid carrier phase of metal oxide compositions.

3. DESCRIPTION OF THE INVENTION

We have discovered that the stability of known colloidal or particulate metal oxide compositions can be significantly increased by adding a stabilizer comprising one or more soluble low molecular weight carbohydrates to the liquid carrier phase of such compositions. The liquid carrier phase may comprise a buffer and a preservative. These carbohydrates are characterized by the fact that a) they are not retained on the surface of the metal oxide based on the equilibrium room temperature dialysis of about 2 milliliters of the metal oxide composition at 0.2M metal concentration against deionized water; and b) they impart sufficient stability to the metal oxide compositions such that the compositions can withstand heat stress without perceptible aggregation. The ability of a colloid to withstand the deleterious effects of storage can be observed over a variety of times and temperatures. A common practice within the pharmaceutical industry is to analyze the stability of a material for short periods of time, and at temperatures above ambient temperature. In this way formulations of greater or lesser stability can be screened and more stable formulations selected. The selection of low molecular weight carbohydrates as stabilizers of metal oxide colloids at elevated temperatures is demonstrated in Tables I and II.

After selection of the most stable compositions from such screening studies, the rate of deterioration of a pharmaceutical can be determined at several different, elevated temperatures. Data concerning the rate of deterioration at various elevated temperatures is obtained and used to calculate the Arrhenius activation energy, which in turn is used to estimate the stability of the pharmaceutical under conditions of storage by a customer, usually 0°–30° C. (See pages 18–31 of "Chemical Stability of Pharmaceuticals: A Handbook for Pharmacists" K. A. Connors, G. L. Amidon and V. J. Stella, Wiley & Sons, New York, 1986 which is incorporated by reference). Thus, the low molecular weight carbohydrate stabilizers of the invention can be assumed to exhibit some degree of stabilizing action for metal oxide colloids when these colloids are stored at any temperature.

The low molecular weight carbohydrates of the invention can be used to stabilize the colloidal materials used as parenterally administered MR contrast agents in U.S. Pat. Nos. 4,770,183 and 4,827,945 incorporated above by reference. These colloidal materials are used to obtain an in vivo MR image of an organ or tissue of an animal or human subject. Preferred colloidal materials used as a parenterally administered MR contrast agent which can be stabilized by the low molecular weight carbohydrates according to this invention are superparamagnetic materials which comprise biodegradable superparamagnetic iron oxides. The biodegradable superparamagnetic iron oxide is characterized by biodegradation in an animal or human subject within about 2 weeks or less after administration, as evidenced by a return of the proton relaxation rates of the organ or tissue to preadministration levels. The biodegradable superparamagnetic iron oxide can be coated by or associated with a high molecular weight polymeric substance such as those discussed below.

The low molecular weight carbohydrates can also be used to stabilize solutions/suspensions of other colloidal or particulate materials that have been used as MR contrast agents, and which have been parenterally administered. These include dextran-magnetite (R. L. Magin et al., Society for Magnetic Resonance in Medicine (1987) P. 538 incorporated herein by reference), magnetic carbohydrate matrix type particles (A. Hemmingsson et al., Acta Radiologica 28:703 705 (1987) incorporated herein by reference), and albumin microspheres (D. J. Widder et al., Amer. J. Roent. 148:399–404 (1987) incorporated herein by reference). Other colloidal or particulate metal oxides in solution/suspension, such as those disclosed in U.S. Pat. Nos. 4,101,435; 4,452,773; 4,795,698; 4,695,392; and 4,501,726, incorporated above by reference, can be stabilized by these low molecular weight carbohydrates as well.

The low molecular weight carbohydrates of the invention can effectively stabilize metal oxide compositions where the metal oxide surface is uncoated or coated by (or unassociated or associated with) a high molecular weight polymer such as dextran having a molecular weight of about 5,000 to about 500,000 daltons, starch having a molecular weight of about 5,000 to about 500,000 daltons, polysaccaride having a molecular weight of about 5,000 to about 500,000 daltons, bovine serum albumin or organosilane.

Representative examples of the metal oxide include, but are not limited to, iron oxide, chromium oxide, cobalt oxide, manganese oxide, iron oxyhydroxide, chromium oxyhydroxide, cobalt oxyhydroxide, manganese oxyhydroxide, chromium dioxide, other transition metal oxides as well as mixed metal oxides. Additionally, the particle size of the metal oxides must necessarily be below 0.8 micron to pass the below-described stability test.

The low molecular weight carbohydrates of the invention preferably have a molecular weight of less than 5,000 daltons, most preferably 1,000 daltons or less. The preferred concentrations of the carbohydrates of the invention which effectively impart stabilization to the carrier phase of the metal oxide composition is in the range of about 0.001M to about 2M, most preferably about 0.05M to about 0.5M.

Some preferred low molecular weight stabilizing agents include, but are not limited to, mannitol, sorbitol, glycerol, inositol, dextran 1 (Pharmacia Inc., Piscataway, N.J.) and ascorbate. In the case of dextran 1, which has a molecular weight of about 1,000 daltons, the same compound can both stabilize the colloid or particulate suspension against unwanted physical changes and block possible adverse reactions. The simultaneous injection of dextran 1 and a complex of dextran and the magnetic iron oxide decreases adverse reactions to high molecular weight dextran alone.

4. EXAMPLES

Experimental examples supporting the use of low molecular weight carbohydrates as stabilizing agents for metal oxide compositions are presented below. Example 1 sets forth one type of stress test for screening useful low molecular weight carbohydrate stability agents. Example 2 examines the ability of various low molecular weight carbohydrates to stabilize colloidal superparamagnetic iron oxide. Example 3 demonstrates that mannitol, taken as representative of the low molecular weight stabilizing agents of the invention, is not retained in association with the metal oxide. As a result, the stabilizing agents of the invention are believed to exert their effects in a manner different from other stabilizing agents which are retained on the metal oxide surface. Example 4 describes the use of low molecular weight carbohydrates to further stabilize colloidal compositions containing a dextran-iron complex which can be used for the treatment of iron-deficiency anemia. Example 5 describes the use of low molecular weight carbohydrates to further stabilize aqueous-based ferrofluids.

4.1 EXAMPLE 1

Stress Test to Screen for Low Molecular Weight Carbohydrate Stabilizing Agents

A convenient stress test for selecting carbohydrates for their ability to stabilize metal oxide colloids or particulate suspensions against undesirable changes in physical state is afforded by autoclaving (i.e. holding at about 121 degrees centigrade for about 30 minutes) the metal oxide in a liquid carrier phase to which the carbohydrate has been added, followed by filtration through a 0.8 micron filter. A fully stabilized metal oxide composition passes through the filter, while compositions undergoing undesirable changes in physical properties are retained on the filter. A designation of "fail" is given to those compositions in which the metal oxides aggregated, producing colored (fully dark brown to black) filters. A designation of "pass" is given to compositions that maintained their physical state and upon filtration yielded colorless or white filters. A designation of "intermediate" is given to those compositions yielding filters that retain significant metal oxide but which exhibit incomplete coverage of the filter.

4.2 EXAMPLE 2

The Ability of Selected Low Molecular Weight Carbohydrates to Stabilize Superparamagnetic Colloids Table I shows the effect of a variety of low molecular weight agents on the filterability of an autoclaved superparamagnetic colloid. The colloid is a superparamagnetic fluid of iron oxide associated with dextran (MW=10,000–15,000 daltons) having 11 milligrams iron per milliliter ("mg Fe/ml") at pH 8.6 prepared according to example 7.10 of U.S. Pat. No. 4,827,945, except that the heating step was omitted in step 7.10.2.

Specifically, five liters of a solution containing 755 grams ("g") $FeCl_3.6H_2O$ and 320 g $FeCl_2.4H_2O$ was added slowly to 5 liters of 16% $NH_4OH$ containing 2500 g dextran (MW=10,000–15,000 daltons). The iron salt solution was added over 5 minutes during which time the base was vigorously stirred during addition. A black magnetic slurry was formed. After centrifugation, the supernatant was diluted to a total volume of 20 liters with deionized sterile water and the resultant solution was dialyzed against ammonium citrate buffer by use of a hollow fiber dialyzer/concentrator, model DC 10 (AMICON Corp., Danvers, Mass.) The ammonium citrate buffer is 10 mM citrate, adjusted to pH 8.2 with $NH_4OH$. The dialyzer cartridge had a 100,000 dalton molecular weight cutoff, permitting removal of dextran. Ultrafiltration was accomplished in a noncontinuous fashion, reducing the volume from 20 to 5 liters and adding 16 liter volumes of solution. Five volumes of 16 liters of deionized, water were added. After this ultrafiltration step, the colloid (39.3 mg Fe/ml) was filtered through a 3 micron filter and then diluted with distilled water to yield a concentration of 11.2 mg Fe/ml.

The low molecular weight agent is then added to the colloid. In most cases the concentration of low molecular weight carbohydrate was 325 mM or about isotonic with blood. The concentration of the low molecular weight carbohydrate in the final stabilized colloid can be from about 0.001M to about 2M.

To perform the test, 10 ml of colloid is autoclaved at 121 degrees centigrade for 30 minutes and then filtered over a 0.8 micron filter (Gelman Sciences Inc., Ann Arbor, Mich.), followed by visual examination of the filter. Filters were rated as described in Example 1 and results are shown in Table I.

TABLE I

| Effect of Low Molecular Agents on Stability of Superparamagnetic Colloid Autoclaved at 121° C. | | |
|---|---|---|
| Agent | Concentration | Colloid Quality |
| water only |  | fail |
| galactose | 325 mM | fail |
| mannose | 325 mM | fail |
| fructose | 325 mM | fail |
| maltose | 325 mM | intermediate |
| sucrose | 325 mM | fail |
| lactose | 325 mM | fail |
| ribose | 325 mM | fail |
| glucosamine | 325 mM | fail |
| dextran 1* | 100 mg/ml | pass |
| acetate | 325 mM | fail |
| PEG-300 | 100 mg/ml | fail |
| threitol | 325 mM | intermediate |
| gluconate | 325 mM | pass/intermediate |
| citrate | 25 mM | pass |
| tartrate | 325 mM | pass |

TABLE I-continued

| Effect of Low Molecular Agents on Stability of Superparamagnetic Colloid Autoclaved at 121° C. | | |
|---|---|---|
| Agent | Concentration | Colloid Quality |
| mannitol | 325 mM | pass |
| sorbitol | 325 mM | pass |
| ascorbate | 325 mM | pass |
| T-10 dextran | 100 mg/ml | fail |
| NaCl | 250 mM | fail |

*Dextran 1 is dextran with a molecular weight of about 1,000 daltons. The solution, supplied for injection by the manufacturer, was diluted from 150 mg/ml, and the final solution contained about 0.06 M NaCl.

Several conclusions can be made from Table I. As expected, based on earlier observations for dextran-associated iron oxide colloids (see FIG. 5 of U.S. Pat. No. 4,827,945), the failure to add a stabilizing agent to the present dextran-associated iron oxide colloid (i.e., water only), resulted in massive, adverse changes in physical state (i.e., failure of the filtration stress test). As demonstrated previously, citrate can stabilize the colloid to autoclaving by being retained on the surface of the iron oxide (i.e. ferric oxyhydroxide, see Col. 28 of U.S. Pat. No. 4,827,945). Addition of polymeric dextran (MW=10,000) was ineffective in stabilizing the colloid, but the addition of dextran 1 was highly effective. No attempt was made to distinguish between the aggregation of the superparamagnetic iron oxide and/or the aggregation (or gelation) of the added stabilizing agent as the cause of poor filtration characteristics.

Linear polyalcohol type compounds stabilized the superparamagnetic colloids, even in cases where the corresponding cyclical hemiacetal monosaccharide was ineffective. This observation was highly unexpected. For example, mannitol passed while mannose failed the stress test. Similarly, the linear polyol acid gluconate gave satisfactory results while closely related monosaccharides like glucose and galactose gave poor results. Two compounds that were not linear polyalcohol type agents gave satisfactory results; they were ascorbate and dextran 1.

The stabilizing effects exerted by the low molecular weight agents of the invention can be observed under a variety of storage conditions, i.e. different times and temperatures. Table II shows an experiment demonstrating that the stabilizing effects of low molecular weight carbohydrates noted at 121° C. (Table I) can also be observed after storage for 3 days at 55° C. In Table II, the colloid of Table I was used and handled in the same manner as in Example 2, except for the heating conditions. Quality was assessed by filtration as described in Example 1.

TABLE II

| Effect of Low Molecular Weight Agents on Stability of Superparamagnetic Colloid At 55° C. | | |
|---|---|---|
| Agent | Concentration | Colloid Quality |
| water | | fail |
| acetate | 325 mM | fail |
| mannose | 325 mM | fail |
| mannitol | 325 mM | pass |

4.3 EXAMPLE 3

The Failure of Mannitol to be Retained On The Surface of Superparamagnetic Iron Oxide To investigate whether the stabilization of superparamagnetic iron oxide involves the retention of the stabilizing agents on the surface of the iron oxide used in Table I, mannitol was selected for study. The retention of mannitol by the superparamagnetic iron oxide was studied by the equilibrium dialysis technique (D. Freifelder "Physical Biochemistry: Applications to Biochemistry and Molecular Biology," W. H. Freeman, San Francisco, 1976 p. 518 incorporated herein by reference). If mannitol is stabilizing the colloid by adsorbing onto the surface of the colloid, $^{14}C$-labelled mannitol should be retained by the superparamagnetic iron oxide colloid when examined by the equilibrium dialysis technique. A membrane with a 12-14 kilodalton cutoff was used which permits mannitol to escape from the bag but retains superparamagnetic iron oxide within the bag.

Three samples were prepared:

A. Superparamagnetic dextran-associated iron oxide colloid (as above), at 11 mg Fe/ml, plus 0.325M mannitol containing 5 microcuries $^{14}C$ mannitol (CFA-238, Amersham Corp., Arlington Heights, Ill.).

B. Mannitol but no superparamagnetic iron oxide.

C. Superparamagnetic dextran-associated iron oxide with mannitol as in sample A but autoclaved at 121 degrees centigrade for 30 minutes.

Samples of approximately 2 mls were placed in an appropriate length of dialysis tubing (Spectra/Por 2, 12,000-14,000 daltons, molecular weight cutoff, Spectrum Medical Industries, Los Angeles, Calif.) and sealed with clips. The samples were then placed into 725 ml of deionized ("DI") water containing a magnetic stirring bar. The samples were dialyzed with gentle stirring using the magnetic stirring bar. After at least 24 hours, a 2 ml sample of dialysate was taken for analysis and the dialysate was replaced with a fresh 725 ml of DI water. In all, three volumes of dialysate were collected. After dialysis was completed, the retentate containing the iron oxide colloid was dissolved in concentrated HCl and brought to 25 mls with DI water. The 2 ml samples of each 725 ml dialysate and a 2 ml sample of retentate were each added to 15 ml of scintillation cocktail (NEF-952, E. I. DuPont de Nemours & Company, Boston, Mass.) and radioactivity determined in a Packard TriCarb Scintillation counter. The results are shown in Table III.

TABLE III

| The Lack of Retention of Mannitol Upon Dialysis With Superparamagnetic Iron Oxide | | | | |
|---|---|---|---|---|
| Sample | | A | B | C |
| Autoclaved | | no | no | yes |
| Volume (ml) | | 2 | 2 | 1.8 |
| Membrane | | 12-14K | 12-14K | 12-14K |
| Dialysate | [a]#1 | 2040875 | 1961488 | 1659163 |
| CPM | #2 | 6525 | 15950 | 7125 |
| | #3 | 383 | 0 | 4500 |
| Total Dialysate | | 2047763 | 1977438 | 1670788 |
| Retantate | | 355 | 6338 | 18375 |
| Total Recovery | | 2048118 | 1983775 | 1689163 |
| Theory[b] | | 195880 | 1905500 | 1647720 |
| % Total[c] | | 105 | 104 | 103 |
| Recovery Retained[d] | | 0.02 | 0.32 | 1.09 |

Sample C was autoclaved at 121° C. for 30 minutes before dialysis.
[a]"#1" represents the first 725 ml volume of DI water; #2 and #3 represent the second and third 725 ml volume of DI water.
[b]"Theory" is the total counts of the sample before dialysis
[c]% Total Recovery = $\frac{\text{total recovery}}{\text{theory}}$
[d]% Retained = $\frac{\text{retentate}}{\text{total recovery}}$ Table III shows the results for the distribution of mannitol between dialysate and retentate. The CPM's are corrected for background. The theoretical value for total counts is based on measurement of a sample before dialysis as described above. The percentage activity remaining in the retentate is based on the total recovered activity.

About 99% or more of the mannitol was present in the dialysate, regardless of whether the colloid was autoclaved (unautoclaved column A, autoclaved column C). When the combination of superparamagnetic colloid and mannitol is subjected to the extreme condition of autoclaving (column C), a small amount of degradation of mannitol results. This is believed to account for the small amount of $^{14}C$ retained in the dialysis bag after autoclaving (1.09%).

Both before and after the temperature and time stress to which the colloid is subjected, there is no formation of a complex between superparamagnetic iron oxide and mannitol. Thus, the low molecular weight carbohydrate stabilizers of the invention do not bind to (or become a coating for) the high molecular weight metal oxide colloid.

The results in Table III indicate that a mannitol-superparamagnetic iron oxide complex does not exist as a definable entity. Rather, the presence of mannitol in the carrier phase changes the properties of the fluid in such a way that the stability of the colloid is enhanced. It should be realized that the binding of mannitol to the superparamagnetic iron oxide colloid can only be ascertained in relation to some experimental technique, which measures binding interactions of equal to or greater than some specific strength, i.e., weaker interactions than can be measured are always possible. The equilibrium dialysis method we have used, (room temperature dialysis of 2 ml colloid at 0.2M iron against a large volume water) is a standard, easy to perform test of association between a colloid (or particle) on the one hand and a low molecular weight stabilizing agent on the other.

Buffers such as Tris and/or preservatives such as phenol can be added in conjunction with the low molecular weight stabilizers that are the subject of this invention.

The inability of mannitol to be retained by the superparamagnetic iron oxide upon dialysis contrasts with the retention of citrate exhibited by the same colloid. We have previously noted the ability of superparamagnetic iron oxide colloids to retain citrate (see Table IV of U.S. Pat. No. 4,827,945).

4.4 EXAMPLE 4

The Ability of Selected Low Molecular Weight Carbohydrates to Stabilize Compositions For The Treatment of Iron-Deficiency Anemia The colloidal therapeutic compositions for the treatment of iron-deficiency aneamia containing, by way of illustration, a dextran-iron complex as disclosed in Herb U.S. Pat. No. 2,885,393 and London, et al. U.S. Pat. No. 2,820,740 and U.S. Pat. No. Re. 24,642, incorporated herein by reference, can be further stabilized by the presence of the low molecular weight carbohydrates of the present invention at concentrations from about 0.001M to about 2M as demonstrated by subjecting such low molecular weight carbohydrate-stabilized composition to either stress test set forth in Example 1 and observing a "passing" result.

4.5 EXAMPLE 5

The Ability of Selected Low Molecular Weight Carbohydrates To Stabilize Aqueous-Based Ferrofluids The aqueous-based ferrofluids, as described, by way of illustration, in Khalafalla, et al. U.S. Pat. No. 4,208,294 and Kelley, U.S. Pat. No. 4,019,994, both incorporated herein by reference, can be further stabilized by the presence of the low molecular weight carbohydrates of the present invention at concentrations from about 0.001M to about 2M as demonstrated by subjecting such low molecular weight carbohydrate-stabilized composition to either stress test set forth in Example 1 and observing a "passing" result.

The compositions disclosed can be varied in a number of ways. The description is intended to illustrate the principles of using the low molecular weight carbohydrate stabilizers for metal oxide colloid and particulate compositions. It is understood that changes and variations can be made therein without departing from the scope of the invention as defined in the following claims.

We claim:

1. An improved MR contrast agent composition parenterally administrable to an animal or human subject, comprising
   (a) a biodegradable superparamagnetic metal oxide coated by or associated with a polymeric substance in a physiologically acceptable carrier, which metal oxide is capable of being biodegraded by said subject within about 2 weeks or less after administration, as evidenced by a return of proton relaxation rates of an affected organ or tissue of said subject to preadministration levels; and
   (b) mannitol at a concentration between about 0.001M and about 2M.

2. An improved parenterally administrable composition, comprising a colloidal or particular biodegradable superparamagnetic metal oxide coated by or associated with a high molecular weight polymeric substance in a physiologically acceptable carrier, which metal oxide is capable of being biodegraded by a subject within about two weeks or less after administration, as evidenced by a return of proton relaxation rates of an affected organ or tissue of said subject to preadministration levels and is filterable through a 0.8 micron filter, wherein the improvement comprises the addition to said carrier of:
   an effective amount of a stabilizer which comprises a physiologically acceptable, soluble, low molecular weight carbohydrate, which carbohydrate
   (a) is not retained on the surface of said metal oxide based on the equilibrium room temperature dialysis of about 2 ml of said composition at 0.2M metal concentration against deionized water; and
   (b) imparts improved physical stability to said composition as determined by heating said composition at about 55° C. for about 3 days and then filtering said composition through a 0.8 micron filter, whereafter substantially no precipitate is visible on said filter.

3. An improved parenterally administrable composition, comprising a colloidal or particular biodegradable superparamagnetic metal oxide coated by or associated with a polymeric substance in a physiologically acceptable carrier, which metal oxide is capable of being biodegraded by a subject within about two weeks or less after administration, as evidenced by a return of proton relaxation rates of an affected organ or tissue of said subject to preadministration levels and is filterable through a 0.8 micron filter, wherein the improvement comprises the addition to said carrier of:

an effective amount of a stabilizer which comprises a physiologically acceptable, soluble, low molecular weight carbohydrate, which carbohydrate (a) is not retained on the surface of said metal oxide based on the equilibrium room temperature dialysis of about 2 ml of said composition at 0.02M metal concentration against deionized water; and (b) imparts improved physical stability to said composition as determined by autoclaving said composition at about 121° C. for about 30 minutes and then filtering said composition through a 0.8 micron filter, whereafter substantially no precipitate is visible on said filter.

4. The composition of claim 2 or 3 wherein said metal is selected from the group consisting of chromium, cobalt, iron, manganese and mixtures thereof.

5. The composition of claim 2 or 3 in which the low molecular weight carbohydrate is present at a concentration of about 0.001M to about 2M.

6. The composition of claim 2 or 3 wherein said low molecular weight carbohydrate has a molecular weight below 5,000 daltons.

7. The composition of claim 6 wherein said low molecular weight carbohydrate is linear polyalcohol carbohydrate.

8. The composition of claim 7 wherein said linear polyalcohol carbohydrate is selected from the group consisting of mannitol, sorbitol and glycerol.

9. The composition of claim 6 wherein said low molecular weight carbohydrate is inositol.

10. The composition of claim 2 or 3 wherein said low molecular weight carbohydrate is dextran having a molecular weight of about 1,000 daltons.

11. The composition of claim 2 or 3 wherein said low molecular weight carbohydrate is mannitol.

12. The composition of claim 2 or 3 wherein said low molecular weight carbohydrate is ascorbate.

13. The composition of claim 2 or 3 in which said carrier comprises a buffer.

14. The composition of claim 2 or 3 in which said carrier further comprises a preservative.

15. The composition of claim 2 or 3 in which said high molecular weight polymer is selected from the group consisting of dextran having a molecular weight of about 5,000 to about 500,000 daltons, starch having a molecular weight of about 5,000 to about 500,000 daltons, polysaccharide having a molecular weight of about 5,000 to about 500,000 daltons, bovine serum albumin and organosilane.

16. The composition of claim 2 or 3 in which said colloid or particulate biodegradable superparamagnetic metal oxide is selected from the group consisting of a dextran-magnetite, a magnetic carbohydrate matrix type particle and an albumin microsphere.

17. The composition of claim 2 or 3 in which said metal is iron.

18. A method for obtaining an in vivo MR image of an organ or tissue of an animal or human subject which comprises parenterally administering to such subject the composition of claim 2 or 3.

19. A method for reducing anemia in an animal or human subject which comprises parenterally administering to such subject the composition of claim 17.

20. A method for stabilizing a biodegradable superparamagnetic metal oxide composition comprising a colloidal or particulate metal oxide coated by or associated with a high molecular weight polymeric substance in a liquid carrier, which metal oxide is capable of being biodegraded by a subject within about two weeks or less after administration, as evidenced by a return of proton relaxation rates of an affected organ or tissue of said subject to preadministration levels and which method comprises adding an effective amount of a stabilizer to said carrier which stabilizer comprises a soluble, low molecular weight carbohydrate, which carbohydrate (a) is not retained on the surface of said metal oxide based on the equilibrium room temperature dialysis of about 2 ml of said composition at 0.2M metal concentration against deionized water; and (b) imparts stability to said composition as determined by heating said composition at about 55° C. for about 3 days and then filtering said composition through a 0.8 micron filter, whereafter o precipitate is visible on said filter.

21. A method for stabilizing a biodegradable superparamagnetic metal oxide composition comprising a colloidal or particulate metal oxide coated by or associated with a high molecular weight polymeric substance in a liquid carrier, which metal oxide is capable of being biodegraded by a subject within about two weeks or less after administration, as evidenced by a return of proton relaxation rates of an affected organ or tissue of said subject to preadministration levels and which method comprises adding an effective amount of a stabilizer to said carrier which stabilizer comprises a soluble, low molecular weight carbohydrate, which carbohydrate (a) is not retained on the surface of said metal oxide based on the equilibrium room temperature dialysis of about 2 ml of said composition at 0.2M metal concentration against deionized water; and (b) imparts stability to said composition as determined by autoclaving said composition at about 121° C. for about 30 minutes and then filtering said composition through a 0.8 micron filter, whereafter no precipitate is visible on said filter.

22. The method of claim 20 or 21 wherein said metal oxide composition is selected from the group consisting of parenterally administrable MR contrast agent compositions, parenterally administrable compositions for reducing anemia and ferrofluids.

* * * * *

UNITED STATES PATENT AND TRADEMARK OFFICE
CERTIFICATE OF CORRECTION

PATENT NO. : 5,102,652

DATED : April 7, 1992

INVENTOR(S) : Groman, et al.

It is certified that error appears in the above-identified patent and that said Letters Patent is hereby corrected as shown below:

In col. 6, line 35, replace "deionized," with --deionized--.

In claim 2, col. 10, line 39, replace "particular" with --particulate--.

In claim 3, col. 10, line 63, replace "particular" with --particulate--.

In claim 7, col. 11, line 29, after "is" insert --a--.

In claim 15, col. 11, line 49, before "dextran" insert --a--.

In claim 15, col. 11, line 50, before "starch" insert --a--.

In claim 15, col. 11, line 52, before "polysaccharide" insert --a--.

In claim 15, col. 11, line 54, before "organosilane" insert --an--.

In claim 20, col. 12, line 30, replace "o" with --no--.

Signed and Sealed this

Third Day of August, 1993

Attest:

MICHAEL K. KIRK

*Attesting Officer*  *Acting Commissioner of Patents and Trademarks*